United States Patent [19]
Ishii et al.

[11] Patent Number: 6,166,264
[45] Date of Patent: Dec. 26, 2000

[54] OXIDATION CATALYST SYSTEM AND METHOD OF OXIDATION WITH THE SAME

[75] Inventors: Yasutaka Ishii, Takatsuki; Tatsuya Nakano, Himeji, both of Japan

[73] Assignee: Daicel Chemical Industries, Ltd., Osaka, Japan

[21] Appl. No.: 09/381,826

[22] PCT Filed: Feb. 10, 1999

[86] PCT No.: PCT/JP99/00566

§ 371 Date: Sep. 24, 1999

§ 102(e) Date: Sep. 24, 1999

[87] PCT Pub. No.: WO99/42211

PCT Pub. Date: Aug. 26, 1999

[30] Foreign Application Priority Data

Feb. 18, 1998 [JP] Japan ................................. 10-054443

[51] Int. Cl.[7] ............................. C07C 45/29; B01J 27/00
[52] U.S. Cl. ...................... 568/471; 502/223; 502/230; 568/424
[58] Field of Search ....................... 502/207, 185, 502/222, 229, 223, 230; 556/136, 137; 568/424, 431, 471, 472

[56] References Cited

FOREIGN PATENT DOCUMENTS

| | | |
|---|---|---|
| 0 237 108 | 9/1987 | European Pat. Off. . |
| 0237108A1 | 9/1987 | European Pat. Off. . |
| 57-48931 | 3/1982 | Japan . |
| 61-65835 | 4/1986 | Japan . |
| 62-223145 | 10/1987 | Japan . |
| 1-305053 | 12/1989 | Japan . |

OTHER PUBLICATIONS

CA:129:202533 abs of Tetrahedron Lett by Hanyu 39(31) pp. 5557–5560, 1998.
CA:115:48976 abs of J Chem Soc Chem Commun by Baeckvall et al (7) pp. 473–5, 1991.
CA:110:153591 abs of Chem Mater. by Stoessel et al 1(2) pp. 259–68, 1989.
CA:121:107581 abs of J Chem Soc Commun by Wang (9) pp. 1037–8, 1994.

*Primary Examiner*—Jean F Vollano
*Attorney, Agent, or Firm*—Birch, Stewart, Kolasch & Birch, LLP

[57] ABSTRACT

The oxidation catalyst system of the invention is composed of (A) a ruthenium compound and (B) a dioxybenzene or its oxidant. The ruthenium compound (A) includes dichlorotris(triphenylphosphine)ruthenium (II) and other ruthenium complexes and Ru/C. The dioxybenzene or its oxidant (B) includes hydroquinone. The oxidation of an alcohol by molecular oxygen in the presence of the oxidation catalyst system can give the corresponding carbonyl compound in high yield. A primary alcohol is more selectively oxidized than a secondary alcohol.

17 Claims, No Drawings

OXIDATION CATALYST SYSTEM AND METHOD OF OXIDATION WITH THE SAME

This application is the national phase under 35 U.S.C. §371 of PCT International Application No. PCT/JP99/00566 which has an International filing date of Feb. 10, 1999 which designated the United States of America.

TECHNICAL FIELD

This invention relates to an oxidation catalyst system which is useful for the production of carbonyl compounds, in particular aldehydes, from alcohols, to a process for the oxidation of alcohols using the oxidation catalyst system, and to a process for the production of carbonyl compounds.

BACKGROUND ART

Oxidizing processes of organic substrates by the use of molecular oxygen as an oxidizing agent, in particular those for oxidizing alcohols to obtain the corresponding carbonyl compounds, are very important in industries of organic chemistry, from the viewpoint of economy and of protecting environment.

Separately, processes for the oxidation of alcohols using a ruthenium compound as a catalyst to give carbonyl compounds have been investigated in different ways. By way of illustration, in J. Chem. Soc., Chem. Commun., 1987, 1625 is proposed a process for the oxidation of an alcohol to give the corresponding carbonyl compound by the use of a catalytic amount of tetrapropylammonium perruthenate and 1.5 equivalents of 4-methylmorpholine-N-oxide with respect to the alcohol. In Bull. Chem. Soc. Jpn., 61, 3607 (1988) is proposed a process for the oxidation of allyl alcohol and benzyl alcohol using dichlorotris (triphenylphosphine)ruthenium(II) and two equivalents of bis (trimethylsilyl)peroxide with respect to the alcohols. These processes, however, require large amounts of co-oxidizing agents such as peroxides which need careful handling, and are economically disadvantageous.

In J. Am. Chem. Soc., 1997, 12661 is disclosed a process for the oxidation of an alcohol by molecular oxygen in the presence of a catalytic amount of tetrapropylammonium perruthenate and a molecular sieve to obtain a carbonyl compound. This process, however, requires comparatively large amounts of molecular sieves. In addition, a secondary alcohol is more liable to be oxidized than a primary alcohol in such oxidation reactions of alcohols by oxygen, and such a primary alcohol can hardly be oxidized in a selective manner (see J. Chem. Soc., Chem. Commun., 1994, 1037).

DISCLOSURE OF INVENTION

It is, therefore, an object of the present invention to provide an oxidation catalyst system and an oxidation process through which an alcohol can be efficiently oxidized by molecular oxygen using a small quantity of a catalyst.

It is another object of the invention to provide a process for the production of carbonyl compounds, through which a carbonyl compound can be obtained from the corresponding alcohol in high yield using a small quantity of a catalyst.

A further object of the invention is to provide a process for the selective oxidation of primary alcohols to obtain the corresponding aldehydes in high yields.

After intensive investigations to achieve the above objects, the present inventors found that a combination use of a ruthenium compound and a specific compound can provide, in a catalytic amount, efficient oxidation of alcohols to give the corresponding carbonyl compounds in satisfactory yields. The present invention has been accomplished based upon the above finding.

To be more specific, the present invention provides an oxidation catalyst system being composed of (A) a ruthenium compound and (B) a dioxybenzene or its oxidant.

The invention further provides a process for oxidation, which includes oxidizing an alcohol by molecular oxygen in the presence of the above oxidation catalyst system.

In addition, the invention provides a process for the production of carbonyl compounds, which includes oxidizing an alcohol by molecular oxygen in the presence of the oxidation catalyst system to give the corresponding carbonyl compound.

BEST MODE FOR CARRYING OUT THE INVENTION

The oxidation catalyst system of the invention comprises (A) a ruthenium compound and (B) a dioxybenzene or its oxidant as catalytic components.

[Ruthenium Compound (A)]

The ruthenium compound (A) includes ruthenium-containing compounds, as well as elementary ruthenium. As examples of the ruthenium compound (A), there may be mentioned metallic ruthenium, ruthenium oxide, ruthenium sulfide, ruthenium hydroxide, ruthenium fluoride, ruthenium chloride, ruthenium bromide, ruthenium iodide, ruthenium sulfate, ruthenic acid or its salts (e.g., ammonium ruthenate), perruthenic acid or its salts (e.g., tetrapropylammonium perruthenate), inorganic ruthenium complexes [e.g., ruthenium hydroxyhalides (such as ruthenium hydroxychloride), hexaammineruthenium halides (such as hexaammineruthenium chloride), nitrosylruthenium, hexahaloruthenic acid or its salts (e.g., sodium hexachlororuthenate)] and other inorganic compounds; ruthenium cyanide, organic ruthenium complexes [e.g., dodecacarbonyltriruthenium(O), dicarbonyltris(triphenylphosphine)ruthenium(II), diacetatodicarbonylbis(triphenylphosphine)ruthenium(II), dichlorotris(triphenylphosphine)ruthenium(II), dihydridotetrakis(triphenylphosphine)ruthenium(II), dichlorobis(acetonitrile)bis(triphenylphosphine)ruthenium(II), ruthenocene] and other organic compounds.

The valence of ruthenium can be any from zero to eight. Ruthenium may preferably be zero-valent to tetravalent, and particularly preferably be divalent.

The preferred ruthenium compounds (A) include metallic ruthenium, perruthenic acid or its salts and ruthenium complexes, among which metallic ruthenium and ruthenium complexes are desirable. Of these compounds, organic ruthenium complexes, in particular organic ruthenium complexes each containing a phosphine such as triphenylphosphine as a ligand [e.g., dichlorotris (triphenylphosphine) ruthenium(II)] are more preferable.

Each of the ruthenium compounds (A) can be used singly or in combination.

[Dioxybenzene or Its Oxidant (B)]

The dioxybenzene (B) includes dioxybenzenes each of which may have a substituent, and equivalents of the aforementioned dioxybenzenes in a dioxybenzene/benzoquinone-redox system. The dioxybenzene includes compounds each comprising a benzene ring and two hydroxyl groups bonded to the benzene ring, as well as dioxypolyphenyl compounds each comprising two hydroxyl groups bonded to different benzene rings. As the dioxybenzene, there may be mentioned, for example, hydroquinone (p-dioxybenzene), catechol (o-dioxybenzene), and dioxybiphenyl.

The substituents which dioxybenzene may have include fluorine, chlorine, bromine and other halogen atoms; cyano group; nitro group; methyl, ethyl, isopropyl, t-butyl and other alkyl groups (preferably, alkyl groups each having about 1 to 4 carbon atoms); trifluoromethyl and other haloalkyl groups (preferably, haloalkyl groups each having about 1 to 4 carbon atoms); hydroxyl group; methoxy, ethoxy and other alkoxy groups (preferably, alkoxy groups each having about 1 to 4 carbon groups); phenoxy and other aryloxy groups; mercapto group; methylthio, ethylthio and other alkylthio groups (preferably, alkylthio groups each having about 1 to 4 carbon atoms); phenylthio and other arylthio groups; acetyl, benzoyl and other acyl groups (preferably, acyl groups each having about 1 to 10 carbon atoms); carboxyl group; methoxycarbonyl, ethoxycarbonyl, phenyloxycarbonyl and other substituted oxycarbonyl groups (preferably, substituted oxycarbonyl groups each having about 2 to 11 carbon atoms); substituted or unsubstituted amino groups; phenyl, naphthyl and other aryl groups and the like. Examples of the dioxybenzene having a substituent also include condensed-ring compounds each having a carbon ring inclusive of a benzene ring or a heterocyclic ring each being condensed to the benzene ring of dioxybenzene.

The term "equivalent in a dioxybenzene/benzoquinone-redox system" means an analogue of dioxybenzene, which can be converted into benzoquinone under oxidation reaction conditions. Such analogues of dioxybenzene include hydroquinone monomethyl ether and other dioxybenzene monoalkyl ethers; hydroquinone dimethyl ether and other dioxybenzene dialkyl ethers; aminophenol; and diaminobenzene. Each of these compounds may have any of the aforementioned substituents. These dioxybenzene analogues are generally converted into benzoquinone by oxidation under acidic conditions.

The preferred dioxybenzenes include hydroquinone, chlorohydroquinone and other hydroquinones each of which may have a substituent (e.g., a halogen atom, an alkyl group, an alkoxy group, a cyano group).

The term "oxidant" of the dioxybenzene means an oxidant corresponding to the dioxybenzene, which constitutes a dioxybenzene/benzoquinone-redox system under oxidation reaction conditions. As examples of the oxidant, there may be mentioned p-benzoquinone (corresponding to hydroquinone), o-benzoquinone (corresponding to catechol), and chlorobenzoquinone (corresponding to chlorohydroquinone).

The dioxybenzene or its oxidant (B) can be used singly or in combination.

The ratio of the dioxybenzene or its oxidant (B) to the ruthenium compound (A) is, for example, such that the former (B)/the latter (A) (by mole) equals about 0.01 to 100, preferably about 0.1 to 10, more preferably about 0.5 to 2 and typically about 0.8 to 1.2.

At least either [e.g., the ruthenium compound (A)] of the ruthenium compound (A) and the dioxybenzene or its oxidant (B) can be supported on a carrier. In particular, when metallic ruthenium is used as the ruthenium compound (A), supporting it on a carrier can substantially increase catalytic activity. The carrier includes conventional carriers for supporting catalysts, such as activated carbon, silica, alumina, silica-alumina and zeolite. The amount of the ruthenium compound (A) falls in the range, for example, from about 0.1% to about 50% by weight, preferably from about 1% to about 20% by weight and more preferably from about 2% to about 10% by weight with respect to the carrier.

[Base]

The oxidation catalyst system of the invention may further comprise a base, in addition to the ruthenium compound (A) and the dioxybenzene or its oxidant (B). The concurrent use of a base often facilitates the oxidation reaction. Examples of such bases include hydroxides, carbonates and hydrogencarbonates of alkali metals (e.g., sodium, potassium), hydroxides and carbonates of alkaline earth metals (e.g., magnesium, calcium), and other inorganic bases; triethylamine, piperidine, N-methylpiperidine, N-methylpyrrolidine, N,N-dimethylaniline and other amines, pyridine, quinoline and other aromatic nitrogen-containing heterocyclic compounds, and other organic bases. The preferred bases include carbonates and hydrogencarbonates of alkali metals, and carbonates of alkaline earth metals, among which potassium carbonate and other carbonates of alkali metals are desirable.

The amount of the base ranges, for instance, from about 0.0001 to about 10 moles, preferably from about 0.001 to about 5 moles, more preferably from about 0.01 to about 1 mole, and typically from about 0.1 to about 0.6 mole, per mole of the ruthenium compound (A).

[Oxidizing Process, and Production Process of Carbonyl Compound]

According to the process of the present invention, an alcohol is oxidized by molecular oxygen in the presence of the aforementioned oxidation catalyst system to give the corresponding carbonyl compound.

The alcohol includes aliphatic alcohols, alicyclic alcohols, aromatic alcohols and heterocyclic alcohols. These alcohols may have plural hydroxyl groups per molecule.

As examples of the aliphatic alcohols, there may be mentioned methanol, ethanol, 1-propanol, 2-propanol, 1-butanol, 2-methylpropanol, 1-pentanol, 1-hexanol, 1-octanol, 2-ethyl-1-hexanol, 1-octanol, 1-decanol, 1-dodecanol, 1-hexadodecanol, 1-octadecanol, allyl alcohol, 3-methyl-2-buten-1-ol, 3,7-dimethyl-2,6-octadien-1-ol (geraniol) and other monohydric alcohols; ethylene glycol, propylene glycol, trimethylene glycol, hexamethylene glycol and other dihydric alcohols; glycerin and other polyhydric alcohols, and other saturated or unsaturated aliphatic alcohols each having about 1 to 30 (preferably about 1 to 20) carbon atoms.

The alicyclic alcohols include, for example, cyclohexanol, cyclohexylmethyl alcohol, 2-cyclohexylethyl alcohol, 10-pinanol, α-pinen-10-ol, 1-hydroxymethyladamantane and other monocyclic or polycyclic alicyclic alcohols. As examples of the aromatic alcohols, there may be mentioned benzyl alcohol, 2-phenylethyl alcohol, 3-phenylpropyl alcohol, 3-phenyl-2-propen-1-ol and other aromatic alcohols each having about 7 to 30 (preferably about 7 to 18) carbon atoms. The heterocyclic alcohols include, for instance, furfuryl alcohol, 2-hydroxymethylthiophene, 2-hydroxymethylpyridine, 3-hydroxymethylpyridine, 4-hydroxymethylpyridine, 2-hydroxymethylquinoline, 1-(3-hydroxypropyl)piperidine, 2-hydroxymethylmorpholine and other alcohols each having a heterocycle containing about 1 to 3 of at least one heteroatom selected from oxygen atom, sulfur atom and nitrogen atom.

These alcohols may have any of various substituents in the molecule. Such substituents include, for example, halogen atoms, substituted oxy groups (e.g., alkoxy groups, cycloalkyloxy groups, aryloxy groups, acyloxy groups, silyloxy groups), mercapto group, substituted thio groups (e.g., alkylthio groups, cycloalkylthio groups, arylthio groups), carboxyl group, substituted oxycarbonyl groups (e.g., alkyloxycarbonyl groups, aryloxycarbonyl groups), substituted or unsubstituted carbamoyl groups, cyano group, acyl group, formyl group, nitro group, substituted or unsubstituted amino groups, alkyl groups, cycloalkyl groups, cycloalkenyl groups, aryl groups and heterocyclic groups.

The molecular oxygen used for the oxidation of alcohol is not especially limited and any of pure oxygen, oxygen diluted with an inert gas such as nitrogen, helium or argon, and air can be used. The amount of molecular oxygen is, generally, 0.5 mole or more (e.g., 1 mole or more), preferably from about 1 to about 100 moles and more preferably from about 1 to about 50 moles, per mole of the alcohol. In general, the molecular oxygen is used in an excess mole with respect to the alcohol.

The amount of the ruthenium compound (A) is, for instance, about 0.001 to 1 mole, preferably about 0.01 to 0.6 mole and more preferably about 0.02 to 0.4 mole, per mole of the alcohol. The amount of the dioxybenzene or its oxidant (B) is, for example, about 0.001 to 1 mole, preferably about 0.01 to 0.6 mole and more preferably about 0.02 to 0.4 mole, per mole of the alcohol. When a base is used, its amount is, for instance, about 0.001 to mole, preferably about 0.005 to 0.2 mole and more preferably about 0.01 to 0.1 mole, per mole of the alcohol.

The reaction may be carried out either in the presence of or in the absence of a solvent. The solvent can be liberally chosen according to, for example, the species of the alcohol and objected product. As examples of the solvent, there may be mentioned benzene, toluene, xylene, ethylbenzene, trifluoromethylbenzene, chlorobenzene, anisole, benzonitrile, nitrobenzene, ethyl benzoate and other benzene derivatives whose benzene ring may be substituted with a halogen atom, an alkyl group, a haloalkyl group, an alkoxy group, cyano group, nitro group, a substituted oxycarbonyl group or the like; hexane, heptane, octane and other aliphatic hydrocarbons; cyclohexane and other alicyclic hydrocarbons; carbon tetrachloride, chloroform, dichloromethane, 1,2-dichloroethane and other haloalkanes; acetone, methyl ethyl ketone and other ketones; methyl acetate, ethyl acetate, isopropyl acetate, butyl acetate and other esters; N,N-dimethylformamide, N,N-dimethylacetamide and other amides; acetonitrile, propionitrile and other nitrites; and diethyl ether, dibutyl ether, dimethoxyethane, dioxane, tetrahydrofuran and other chain or cyclic ethers. The preferred solvents include benzene, toluene, trifluoromethylbenzene and the other benzene derivatives, 1,2-dichloroethane and other haloalkanes, ethyl acetate and other esters. Of these compounds, trifluoromethylbenzene and other benzene derivatives whose benzene ring is substituted with a haloalkyl group are desirable. Each of these solvents can be employed independently or in combination.

The reaction temperature can be liberally chosen according to, for instance, the species of the alcohol and is, for example, about 0° C. to 200° C., preferably about 10° C. to 100° C., and more preferably about 30° C. to 80° C. The reaction can be conducted at atmospheric pressure or under pressure. It may also be carried out in any systems inclusive of batch system, semi-batch system and continuous system.

According to the process of the invention, an oxidation reaction can proceed smoothly even in the presence of a small quantity of a catalyst to give the corresponding carbonyl compound in satisfactory yield. In addition, the present invention is specifically characterized in that a primary alcohol is selectively oxidized. Therefore, an aldehyde corresponding to a primary alcohol can be obtained in high yield from a mixture of the primary alcohol and a secondary alcohol. Upon the oxidation of a compound having both hydroxyl groups corresponding to a primary alcohol and a secondary alcohol in the molecule, the hydroxyl group corresponding to the primary alcohol is selectively oxidized to give the corresponding aldehyde in high yield. According to the invention, even when an alcohol having a hydroxyl group in so-called allyl-position or benzyl-position is oxidized, the corresponding unsaturated aldehyde or aromatic aldehyde can be formed in high yield without any by-produced saturated compounds due to intramolecular hydrogen transfer.

A carbonyl compound formed through the reaction can readily be isolated and purified by a conventional isolation and purification means including filtration, condensation, distillation, extraction, crystallization, recrystallization or column chromatography, or any combination of these isolation means.

According to the oxidation catalyst system and oxidizing process of the present invention, an alcohol can efficiently be oxidized by molecular oxygen with the use of a small quantity of a catalyst.

The production process of the invention provides a carbonyl compound from the corresponding alcohol in high yield with the use of a small quantity of a catalyst. In addition, a primary alcohol is selectively oxidized to give the corresponding aldehyde in high yield.

The present invention will be further illustrated in detail with reference to several examples below which are not directed to limiting the scope of the invention.

EXAMPLE 1

To a mixture of 0.2 millimole of $Ru(PPh_3)_3Cl_2$ [dichlorotris(triphenylphosphine)ruthenium(II)], 0.2 millimole of hydroquinone, 0.03 millimole of potassium carbonate and 6 ml of trifluoromethylbenzene was added 1 millimole of 1-decanol, and the resultant mixture was stirred under oxygen atmosphere (1 atm) at 60° C. for 20 hours. The products were subjected to chromatography on silica gel (eluent: hexane/ethyl acetate=10/1) for the isolation to give 1-decanal in a conversion rate of 1-decanol of 90% (yield 90%).

EXAMPLE 2

The procedure of Example 1 was repeated, except that 6 ml of benzene was used instead of trifluoromethylbenzene, to give 1-decanal in a conversion rate of 1-decanol of 86% (yield 78%).

EXAMPLE 3

The procedure of Example 1 was repeated except that 6 ml of 1,2-dichloroethane was used instead of trifluoromethylbenzene to give 1-decanal in a conversion rate of 1-decanol of 70% (yield 65%).

EXAMPLE 4

By using 6 ml of ethyl acetate instead of trifluoromethylbenzene, 1-decanal was obtained in a conversion rate of 1-decanol of 60% (yield 59%) in the same manner as in Example 1.

EXAMPLE 5

The procedure of Example 1 was repeated, except that 0.2 millimole of $Pr_4N^+RuO_4^-$ [tetrapropylammonium perruthenate (TPAP)] was used instead of Ru(PPh$_3$)$_3$Cl$_2$, to give 1-decanal in a conversion rate of 1-decanol of 98% (yield 40%).

EXAMPLE 6

The procedure of Example 1 was repeated, except that 0.2 millimole (in terms of Ru) of 5% by weight Ru/C was used instead of Ru(PPh$_3$)$_3$Cl$_2$, to give 1-decanal in a conversion rate of 1-decanol of 93% (yield 68%).

EXAMPLE 7

The procedure of Example 1 was repeated, except that a mixture of 1-decanol (0.5 millimole) and 4-decanol (0.5 millimole) was used instead of 1-decanol, to give 1-decanal (yield 83%), and 4-decanone (yield 3%).

EXAMPLE 8

The procedure of Example 1 was repeated, except that 1 millimole of 1-octanol was used instead of 1-decanol, to give 1-octanal in a conversion rate of 1-octanol of 89% (yield 89%).

EXAMPLE 9

The procedure of Example 1 was repeated, except that 1 millimole of cyclohexylmethyl alcohol was used instead of 1-decanol, to give cyclohexanecarbaldehyde in a conversion rate of cyclohexylmethyl alcohol of 58% (yield 48%).

EXAMPLE 10

The procedure of Example 1 was repeated except that 1 millimole of 10-pinanol was used instead of 1-decanol to give 10-pinanal in a conversion rate of 10-pinanol of 80% (yield 76%).

EXAMPLE 11

The procedure of Example 1 was repeated, except that 1 millimole of 1-hydroxymethyladamantane was used instead of 1-decanol and 6 ml of 1,2-dichloroethane was employed in lieu of trifluoromethylbenzene, to give 1-adamantanecarbaldehyde in a conversion rate of 1-hydroxymethyladamantane of 76% (yield 58%).

EXAMPLE 12

To a mixture of 0.1 millimole of Ru(PPh$_3$)$_3$Cl$_2$ [dichlorotris(triphenylphosphine)ruthenium(II)], 0.1 millimole of hydroquinone, 0.03 millimole of potassium carbonate and 6 ml of trifluoromethylbenzene was added 1 millimole of benzyl alcohol, and the resultant mixture was stirred under oxygen atmosphere (1 atm) at 50° C. for 15 hours. The products were subjected to chromatography on silica gel (eluent: hexane/ethyl acetate=10/1) for the isolation to give benzaldehyde in a conversion rate of benzyl alcohol of 80% (yield 80%).

EXAMPLE 13

The procedure of Example 12 was repeated, except that 1 millimole of 3-methyl-2-buten-1-ol was used instead of benzyl alcohol, to give 3-methyl-2-butenal in a conversion rate of 3-methyl-2-buten-1-ol of 94% (yield 81%).

EXAMPLE 14

The procedure of Example 12 was repeated, except that 1 millimole of geraniol was used instead of benzyl alcohol, to give geranial in a conversion rate of geraniol of 99% or more (yield 98%).

EXAMPLE 15

The procedure of Example 12 was repeated, except that 1 millimole of α-pinen-10-ol was used instead of benzyl alcohol, to give α-pinen-10-al in a conversion rate of α-pinen-10-ol of 92% (yield 90%).

EXAMPLE 16

The procedure of Example 12 was repeated, except that 1 millimole of 3-phenyl-2-propen-1-ol was used instead of benzyl alcohol, to give 3-phenyl-2-propenal in a conversion rate of 3-phenyl-2-propen-1-ol of 100% (yield 99%).

What is claimed is:

1. An oxidation catalyst system comprising (A) a ruthenium compound, (B) a dioxybenzene or its oxidant and (C) a base.

2. A process for oxidation, comprising the step of:
    oxidizing an alcohol by molecular oxygen in the presence of the oxidation system according to claim 1.

3. A process for the production of carbonyl compounds, comprising the step of:
    oxidizing an alcohol by molecular oxygen in the presence of the oxidation system according to claim 1 to give the corresponding carbonyl compound.

4. The process for the production of carbonyl compounds according to claim 3, wherein a primary alcohol is oxidized to give the corresponding aldehyde.

5. An oxidation catalyst system according to claim 1, wherein said ruthenium compounds are selected from the group consisting of metallic ruthenium, perruthenic acid or its salts, inorganic or organic ruthenic complexes, and mixtures thereof.

6. The oxidation catalyst system according to claim 5, wherein said organic ruthenium complex contains a phosphine as a ligand.

7. The oxidation catalyst system according to claim 1, wherein said dioxybenzene or its oxidants are selected from the group consisting of substituted or unsubstituted hydroquinone, substituted or unsubstituted catechol, substituted or unsubstituted dioxybiphenyl, substituted or unsubstituted dioxybenzene monoalkyl ethers, substituted or unsubstituted dioxybenzene dialkyl ethers, substituted or unsubstituted aminophenol and substituted or unsubstituted diaminobenzene.

8. An oxidation catalyst system according to claim 7, wherein the substituents are selected from the group consisting of halogen atoms, cyano group, nitro group, alkyl groups having 1 to 4 carbon atoms, haloalkyl groups having 1 to 4 carbon atoms, hydroxyl group, alkoxy groups having 1 to 4 carbon atoms, aryl oxy groups, mercapto group, alkylthio groups having 1 to 4 carbon atoms, arylthio groups, acyl groups having 1 to 10 carbon atoms, carboxyl groups, substituted oxycarbonyl groups having 2 to 11 carbon atoms, substituted or unsubstituted amino groups and aryl groups.

9. An oxidation catalyst system according to claim 1, wherein the ratio by moles of the dioxybenzene or its oxidant (B) to ruthenium compound (A) is about 0.01 to 100.

10. An oxidation catalyst system according to claim 1, wherein the ratio by moles of the dioxybenzene or its oxidant (B) to ruthenium compound (A) is about 0.1 to 10.

11. An oxidation catalyst system according to claim 1, wherein the ratio by moles of the dioxybenzene or its oxidant (B) to ruthenium compound (A) is about 0.5 to 2.

12. An oxidation catalyst system according to claim 1, wherein the ratio by moles of the dioxybenzene or its oxidant (B) to ruthenium compound (A) is about 0.8 to 1.2.

13. An oxidation catalyst system according to claim 1, wherein a carrier supports the ruthenium compound (A), said carrier is selected from the group consisting of activated carbon, silica, alumina, silica-alumina and zeolite.

14. An oxidation catalyst system according to claim 13, wherein the amount of the ruthenium compound (A) is from about 0.1% to about 50% by weight with respect to the carrier.

15. An oxidation catalyst system according to claim 1, wherein said base (C) is selected from the group consisting of hydroxides, carbonates and hydrogencarbonates of alkali metals, amines, and nitrogen-containing heterocyclic compounds; and said base is present in the amount of from about 0.0001 to 10 moles per mole of the ruthenium compound (A).

16. An oxidation catalyst system according to claim 1, wherein the ratio by moles of the base (C) to ruthenium compound (A) is about 0.0001 to 10.

17. The process of oxidation according to claim 2, wherein the ratio by moles of the ruthenium compound (A) to the alcohol is about 0.001 to 1, the ratio by moles of the dioxybenzene or its oxidant (B) to alcohol is about 0.001 to 1, and the ratio by moles of the base (C) to the alcohol is about 0.001 to 1.

\* \* \* \* \*